United States Patent [19]
Dandekar et al.

[11] Patent Number: 5,449,696
[45] Date of Patent: Sep. 12, 1995

[54] PROCESS FOR METHANOL PRODUCTION USING SIMULATED MOVING BED REACTIVE CHROMATOGRAPHY

[75] Inventors: Hemant W. Dandekar, Chicago; Gregory A. Funk, Carol Stream, both of Ill.

[73] Assignee: UOP, Des Plaines, Ill.

[21] Appl. No.: 283,890

[22] Filed: Aug. 1, 1994

[51] Int. Cl.[6] .................... C07C 27/06; C07C 29/15
[52] U.S. Cl. ............................. 518/706; 518/712; 518/713
[58] Field of Search .............. 518/706, 713, 712; 568/913

[56] References Cited

U.S. PATENT DOCUMENTS

| | | | |
|---|---|---|---|
| 4,731,387 | 3/1988 | Westerterp | 518/706 |
| 4,908,390 | 6/1990 | Matros et al. | 518/706 |
| 4,968,722 | 11/1990 | Westerterp | 518/706 |
| 5,216,034 | 3/1993 | Sie | 518/706 |

FOREIGN PATENT DOCUMENTS

| | | | |
|---|---|---|---|
| 2233329 | 9/1991 | United Kingdom | C07C 29/15 |
| 2255516 | 11/1992 | United Kingdom | B01J 8/28 |

*Primary Examiner*—Werren B. Lone
*Attorney, Agent, or Firm*—Thomas K. McBride; Eugene I. Snyder

[57] ABSTRACT

A process for the continuous production of methanol through contacting at least one feed stream containing at least carbon monoxide and hydrogen, and optionally carbon dioxide, with a simulated moving bed acting as a catalyst for methanol synthesis and an adsorbent for the methanol formed has been developed. The carbon monoxide and hydrogen are catalytically reacted to form methanol which is separated from the carbon monoxide and hydrogen by concurrent adsorption. The methanol is desorbed using a carbon dioxide or hydrogen desorbent and collected. A specific embodiment is one where the feed stream is introduced to the simulated moving bed at a temperature from about 210° to about 270° C. and the desorbent is introduced to the simulated moving bed at a temperature of about 150° to about 250° C.

22 Claims, 2 Drawing Sheets

PROCESS FOR METHANOL PRODUCTION USING SIMULATED MOVING BED REACTIVE CHROMATOGRAPHY

BACKGROUND OF THE INVENTION

Methanol production is typically accomplished by direct hydrogenation of carbon monoxide and, to a lesser extent, carbon dioxide according to the following equations:

$$CO + 2H_2 \rightleftharpoons CH_3OH$$

$$CO_2 + 3H_2 \rightleftharpoons CH_3OH + H_2O$$

These reactions are most commonly carried out by contacting the carbon monoxide, carbon dioxide and hydrogen reactants with a fixed bed of catalyst. Unfortunately, in fixed bed systems, conversion yields are generally in the range of only 15 to 30% due to equilibrium limitations. Consequently, large volumes of unconverted reactants must be recycled to the reactor. Applicants and others have investigated alternate systems to increase the single pass conversion and to decrease or eliminate reactant recycle.

U.S. Pat. No. 4,731,387 discloses a method of producing methanol using a reaction zone of a fixed bed of catalyst particles with interstices between the particles. Fine particles capable of adsorbing substantially all of the methanol product are passed in a downward direction through the interstices. The fine particles adsorb the methanol and are ultimately withdrawn from the reaction zone. Methanol is desorbed and recovered from the particles that were withdrawn from the reaction zone. Through adsorbing and removing the methanol product from the reaction zone, a high driving force for the reaction towards methanol production is maintained and conversion yields are increased.

U.S. Pat No. 4,968,722 discloses a similar methanol production process using a fixed bed of catalyst particles with a liquid flowing through the bed to absorb methanol. The patent teaches that it is expected that the liquid film will cause mass transfer resistances at the catalyst surface and especially inside the pores resulting in a loss of catalyst activity. Therefore, the stated preferred embodiment is one where the fixed bed of catalyst is in a reaction zone which is connected to an absorption zone where the methanol is absorbed. The system may consist of a single reaction zone, the effluent of which is passed through a single absorption zone to remove methanol before being recycled to the reaction zone, or a plurality of reaction zones with the effluent of each reaction zone being passed through an absorption zone for methanol removal before continuing to the next successive reaction zone.

U.K. Patent Application 2,255,516A discloses a methanol production process using a plurality of fluidized bed catalytic reactors in series and an inert solvent to absorb methanol from the reaction mixture. Between consecutive fluidized bed reactors a facility is present to effect intimate contact between the inert solvent and the methanol-containing reaction mixture so that the methanol is absorbed by the inert solvent and the methanol-depleted reaction mixture is conducted to the next successive fluidized bed reactor. The methanol is recovered from the inert solvent through flashing and subsequent distillation. The application teaches that suitable inert solvents are water, higher alcohols, higher esters, and higher ethers.

U.K. Patent Application 2,344,329A discloses a methanol production process where synthesis gas is produced and fed to a conventional methanol synthesis reactor where a portion of the synthesis gas is convened to methanol which is collected. A very large purge gas stream from the conventional reactor is then conducted to a cyclically operated vessel containing a mixture of methanol synthesis catalyst and methanol adsorbent. In this vessel, as methanol is formed it is adsorbed, thus removing it from the reactants and promoting more methanol to be formed. When the adsorbent is saturated with methanol, the vessel is taken offline and the methanol desorbed by depressurizing or sweeping with methane. The desorbed methanol is combined with the methanol collected from the conventional reactor.

Applicants' invention is significantly different from tile disclosures of the prior art. For example, applicants use a mixture of a methanol synthesis catalyst and a methanol adsorbent in a simulated moving bed mode. The mixture allows the methanol to be adsorbed immediately upon its formation, thereby removing the menthanol from the reactants and permitting the formation of methanol to continue. The simulated moving bed provides a process for not only synthesizing and adsorbing methanol, but also for desorbing the separated methanol using a desorbent, all within the same system. Furthermore, since the methanol is desorbed while still in the presence of the catalyst, specific desorbents may be chosen which aid in suppressing the back reaction of methanol to carbon monoxide, carbon dioxide, and hydrogen. Additionally, two suitable desorbents are reactants themselves, facilitating the increased conversion and eliminating the need for an inert desorbent. The desorbent also may be introduced to the simulated moving bed at a temperature which quenches the back reaction of methanol to carbon monoxide, carbon dioxide, and hydrogen.

SUMMARY OF THE INVENTION

The purpose of this invention is to provide a process; for the continuous production of methanol through contacting at least one feed stream containing at least carbon monoxide and hydrogen with a simulated moving bed acting as a catalyst for methanol synthesis and an adsorbent for the methanol formed. The carbon monoxide and hydrogen are catalytically reacted to form methanol which is separated from the carbon monoxide and hydrogen by adsorption. The methanol is desorbed using a carbon dioxide, hydrogen, or methane desorbent and collected. A specific embodiment of the invention is one where the feed stream is introduced to the simulated moving bed at a temperature from about 210 to about 270° C. and the desorbent is introduced to the simulated moving bed at a temperature of about 150 to about 250° C. Another specific embodiment is one where the feed stream also contains carbon dioxide.

Another specific embodiment is one where (1) a methane-containing stream is passed to a desulfurization zone to form a desulfurized methane-containing stream which is depleted in hydrogen sulfide; (2) the desulfurized methane-containing stream is passed to a steam reforming zone where the methane is reacted with water to form carbon monoxide and hydrogen, and a portion of the carbon monoxide is further reacted with water to form carbon dioxide and hydrogen, resulting in a stream containing at least carbon monoxide, carbon dioxide, hydrogen, and water; (3) the stream containing at least carbon monoxide, carbon dioxide, hydrogen, and water is passed to a condensation zone to remove water, resulting in a water-depleted stream containing at least carbon monoxide, carbon dioxide and hydrogen; (4) the water-depleted stream containing at least carbon monoxide, carbon dioxide, and hydrogen is passed to a compression zone to afford a pressurized stream containing at least carbon monoxide, carbon dioxide, and hydrogen; (5) the pressurized stream containing at least carbon monoxide, carbon dioxide, and hydrogen and a stream containing a desorbent selected from the group consisting of carbon dioxide, hydrogen, and methane are passed to a methanol synthesis zone of a simulated moving bed to produce two streams, a stream containing methanol and desorbent and a stream containing at least hydrogen and desorbent; (6) the stream containing methanol and desorbent is passed to a separation zone to produce two streams, a stream enriched in methanol and a stream enriched in desorbent; and (7) the stream enriched in methanol is collected.

Still another specific embodiment of the invention is one where (1) a methane-containing stream is passed to a desulfurization zone to form a desulfurized methane-containing stream which is depleted in hydrogen sulfide; (2) the desulfurized methane-containing stream is divided into two portions, the first portion being passed to a steam reforming zone where the methane is reacted with water to form carbon monoxide and hydrogen, and a portion of the carbon monoxide is reacted with water to form carbon dioxide and hydrogen, resulting in a steam reforming zone effluent containing a mixture of carbon monoxide, carbon dioxide, hydrogen, and water which is combined with the second portion of the desulfurized methane-containing stream to form a stream containing methane, carbon monoxide, carbon dioxide, hydrogen, and water; (3) the stream containing methane, carbon monoxide, carbon dioxide, hydrogen, and water and a stream containing oxygen are passed to a catalytic reforming zone where methane is reacted with oxygen to form carbon monoxide and hydrogen to afford a stream containing at least carbon monoxide, carbon dioxide, hydrogen, and water which has a hydrogen to carbon molecular ratio in the range of about 2.0:1 to about 2.5:1; (4) the stream containing at least carbon monoxide, carbon dioxide, hydrogen, and water is passed to a condensation zone to remove water, resulting in a water-depleted stream containing at least carbon monoxide, carbon dioxide and hydrogen; (5) the water-depleted stream containing at least carbon monoxide, carbon dioxide, and hydrogen is passed to a compression zone to afford a pressurized stream containing at least carbon monoxide, carbon dioxide, and hydrogen; (6) the pressurized stream containing at least carbon monoxide, carbon dioxide, and hydrogen, and a stream containing a desorbent selected from the group consisting of carbon dioxide, hydrogen, and methane are passed to a methanol synthesis zone of a simulated moving bed to produce two streams, an extract stream containing methanol and desorbent, and a raffinate stream containing at least hydrogen and desorbent; (7) the stream containing methanol and desorbent is passed to a separation zone to produce two streams, a stream enriched in methanol and a stream enriched in desorbent; and (8) the stream enriched in methanol is collected.

Yet another specific embodiment is one where (1) a methane-containing stream is passed to a desulfurization zone to form a desulfurized methane-containing stream which is depleted in hydrogen sulfide; (2) the desulfurized methane-containing stream is passed to a steam reforming zone where the methane is reacted with water to form carbon monoxide and hydrogen, and a portion of the carbon monoxide is reacted with water to form carbon dioxide and hydrogen, resulting in a stream containing at least carbon monoxide, carbon dioxide, hydrogen, and water; (3) the stream containing at least carbon monoxide, carbon dioxide, hydrogen, and water is passed to a condensation zone to remove water, resulting in a water-depleted stream containing at least carbon monoxide, carbon dioxide and hydrogen; (4) the water-depleted stream containing at least carbon monoxide, carbon dioxide, and hydrogen is passed to a compression zone to afford a pressurized stream containing at least carbon monoxide, carbon dioxide, and hydrogen; (5) the pressurized stream containing at least carbon monoxide, carbon dioxide, and hydrogen is passed to a first separation zone to afford a first stream enriched in hydrogen and a stream enriched in carbon monoxide and hydrogen having a hydrogen to carbon molecular ratio of from about 2.0:1 to about 2.5:1; (6) the first stream enriched in hydrogen and the stream enriched in carbon monoxide and hydrogen are passed to a methanol synthesis zone of a simulated moving bed to produce two streams, a stream containing methanol and hydrogen, and a second stream containing hydrogen; (7) the stream containing methanol and hydrogen is passed to a second separation zone to produce two streams, a stream enriched in methanol and a third stream enriched in hydrogen; and (8) the stream enriched in methanol is collected.

Still another specific embodiment of the invention is one where (1) a naphtha-, fuel oil-, or coal-containing stream and an oxygen-containing stream are passed to a partial oxidation zone to form a stream containing at least carbon monoxide and hydrogen; (2) the stream containing at least carbon monoxide and hydrogen is passed to a desulfurization zone to form a desulfurized stream containing carbon monoxide and hydrogen which is depleted in hydrogen sulfide; (3) the desulfurized stream containing at least carbon monoxide and hydrogen is passed to a shift conversion reaction zone where at least a portion of the carbon monoxide is reacted with water to form carbon dioxide and hydrogen thereby forming a stream of at lest carbon monoxide, carbon dioxide, hydrogen, and water; (4) the stream containing at least carbon monoxide, carbon dioxide, hydrogen, and water is passed to a condensation zone to remove water, resulting in a water-depleted stream containing at least carbon monoxide, carbon dioxide and hydrogen; (5) the water-depleted stream containing at least carbon monoxide, carbon dioxide, and hydrogen is passed to a compression zone to afford a pressurized stream containing at least carbon monoxide, carbon dioxide, and hydrogen; (6) the pressurized stream containing at least carbon monoxide, carbon dioxide, and hydrogen is passed to a first separation zone to afford a first stream enriched in carbon dioxide and a stream enriched in a carbon monoxide and hydrogen mixture having a hydrogen to carbon molecular ratio of from about 2.0:1 to about 2.5:1; (7) the first stream enriched in carbon dioxide and the stream enriched in carbon monoxide arid hydrogen are passed to a methanol synthesis zone of a simulated moving bed to produce two streams, a stream containing methanol and carbon dioxide, and a second stream containing hydrogen and carbon dioxide; (8) the stream containing methanol and carbon dioxide is passed to a second separation zone to produce two streams, a stream enriched in methanol and a second stream enriched in carbon dioxide; and (9) the stream enriched in methanol is collected.

BRIEF DESCRIPTION OF THE DRAWING

The drawings have been simplified by the deletion of a large number of pieces of apparatus customarily employed in processes of this nature which are not specifically required to illustrate the performance of the subject invention.

DETAILED DESCRIPTION OF THE INVENTION

The invention is a process of continuously producing methanol using a simulated moving bed to effect reactive chromatography, i.e., a process where a simulated moving bed both catalyzes the reaction of carbon monoxide and hydrogen to form methanol and effects the separation of the methanol product from the reactants. In general terms, the carbon monoxide and hydrogen reactants are contacted with a simulated moving bed of particulate solids. The bed is effective both to catalyze methanol synthesis and to separate the methanol product from the reactants through adsorption of the methanol. The now separated methanol is desorbed by a carbon dioxide or hydrogen desorbent and continuously removed from the simulated moving bed and collected. Continuously removing methanol promotes the reaction to continue and form additional methanol. The process continues in this fashion, with methanol being retained by the adsorbing properties of the simulated moving bed, thus allowing continued reaction of the carbon monoxide and hydrogen.

Both reactive chromatography and simulated moving bed technology are known in the art, and a general discussion of these technologies may be found in Mowry, J. R. In *Handbook of Petroleum Refining Processes*; Meyers, R. A. Ed.; McGraw-Hill: New York, 1986; pp 8-79 to 8-99 for the simulated moving bed technique; and *Preparative and Production Scale Chromatography*; Ganetsos, G., Barker, P. E., Eds.; Chromatographic Science Series Vol. 61; Marcel Dekker: New York, 1993; Chapters 16-21 for reactive chromatography. Applicants have realized that these technologies may be effectively applied to the hydrogenation of carbon monoxide or carbon dioxide to form methanol, and the details of reactive chromatography and simulated moving bed technique as applied to the instant invention are supplied below.

Reactive chromatography requires that the desired reaction and the separation of the products and reactants occur concurrently. Therefore, the simulated moving bed of the present invention must perform dual functions. The mixture of solids forming the simulated moving bed must be effective as a catalyst for methanol synthesis and also must be effective as an adsorbent which preferentially retains methanol in order to separate the methanol from the reactants. When the reactants enter the bed and contact the mixture of solids, the hydrogenation reaction is catalyzed and methanol is formed. The hydrogenation reaction primarily takes place in the portion of the solid bed adjacent to and immediately downstream in the direction of the fluid flow of the introduction point of the feed stream which contains at least carbon monoxide and hydrogen, and optionally carbon dioxide. Not all of the reactants will immediately react. Since the mixture of solids is also effective as an adsorbent for the reactants, the product and reactants begin to undergo separation. The reactants which are less strongly adsorbed by the adsorbent are carried with the fluid flow, and methanol, which is strongly adsorbed by the adsorbent, is carried countercurrently with the simulated movement of the solids. The migration of the methanol and reactants in opposite directions results in one region richer in methanol and the other region leaner in methanol. Once separated, the reactants carried by the fluid flow are removed from the region leaner in methanol in a raffinate stream and collected. Concurrently, the methanol carried by the adsorbent is desorbed at the region richer in methanol by the introduction of a desorbent. The desorbed methanol, still being in contact with the simulated moving bed, may be catalytically reacted back to form carbon monoxide and hydrogen. For this reason, the desorbent may be specifically chosen to be either carbon dioxide or hydrogen in order to suppress the back reaction. The excess hydrogen shifts the equilibrium of the reaction, and it is believed that the carbon dioxide obstructs the active sites of the catalyst. the back reaction also may be suppressed through temperature control, in which case methane is an additional desorbent choice. The process operates continuously with the reactants being introduced, the hydrogenation being catalyzed, and the product being separated from reactants and collected, thereby allowing the hydrogenation reaction to continue. Due to the continuous separation and removal of the methanol, the thermodynamic equilibrium characteristic of a static system is no longer a limiting factor and the hydrogenation continues, resulting in a greater ultimate yield of methanol. As a result, external recycle of unconsumed reactants is greatly reduced or eliminated resulting in a substantial savings in operating costs.

As previously discussed, the simulated moving bed is made up of a mixture of particulate solids which together are effective to both catalyze the hydrogenation reaction and to separate the methanol from the reactants. Two or more solids, at least one being a methanol synthesis catalyst and at least one being an adsorbent, are used as a homogeneous mixture. A wide variety of solid catalysts anti adsorbents are available, and each particular feed composition and corresponding desorbent may require a different combination of solids. The solid or solids acting as a catalyst may be any of the commonly used methanol synthesis catalysts including, but not limited to, the mixtures of zinc oxide-chromium trioxide, copper-zinc oxide-chromium trioxide, copper-zinc oxide, copper-zinc oxide-aluminum trioxide, copper oxide-zinc oxide-aluminum trioxide, and zinc-chromium trioxide. Methanol synthesis catalyst mixtures and their ratios are very well known and do not require discussion here; for reference, see *Rate Equations of Solid-Catalyzed Reactions*; Mezaki, R., Inoue, H., Eds.; Univ. Tokyo Press: Tokyo, 1991; pp. 27-36. The adsorbent solid or solids are selected to either have a pore size capable of admitting methanol but not carbon monoxide or hydrogen, or an affinity for methanol.

Examples of suitable adsorbents include, but are not limited to, aluminum trioxide, silica gel, 3A-, 4A-, 5A-, X-, and Y-type zeolites, ferrurite, ZSM-5, high aluminum MCM-41, and activated carbon. Depending upon the composition of the feed, several different adsorbents may be combined in order to accomplish the separation function. Different applications may require different ratios of catalyst to adsorbent or different catalyst and adsorbent combinations. For example, when hydrogen is used as the desorbent, the adsorbent preferably should be chosen to be 3A-type zeolite. When carbon dioxide is used as the desorbent, a preferred adsorbent is activated alumina, and when methane is used as the desorbent, 5A-type zeolite is the preferred adsorbent. Typically, the catalyst to adsorbent ratio is in the range of about 1:9 to about 9:1 with a preferred range of from about 1:1 to about 1:5.

The catalyst and adsorbent mixture of solids, once chosen, is used in the process in the form of a simulated moving bed where the bed is held stationary, and the locations at which the various streams enter and leave the bed are periodically moved. The bed itself is usually a succession of fixed sub-beds, and different systems may require differing numbers of sub-beds. The most commonly used range is from about 4 sub-beds to about 24 sub-beds, with the preferred range being from 6 to 24 sub-beds, and the most preferred range being from 6 to 8 sub-beds. The sub-beds may be housed in individual interconnected chambers, each equipped with an inlet and an outlet line. Alternately, the sub-beds may be housed in a single chamber with each sub-bed being equipped with an inlet and an outlet line. The hydrogenation reaction is strongly exothermic ($\Delta H_{298} = -91$ KJ/mol) and the increased temperature both unfavorably influences the position of the reaction equilibrium and accelerates the deactivation of the catalyst. Therefore, a preferred embodiment of the invention incorporates controls to minimize the temperature increase. For example, in the case where the sub-beds are housed in individual interconnected chambers, interstage heat exchangers may be used to remove excess heat from sub-bed effluents before the effluent is passed to the next sub-bed. Another temperature control technique involves controlling the temperature of multiple feed streams introduced throughout the reaction zone and is discussed in greater detail below.

The shift in the locations of input and output streams in the direction of the fluid flow through the bed simulates the movement of the solid bed in the opposite direction. Commercially, moving the locations of the input and output streams may be accomplished by a variety of fluid-directing devices such as rotary valves or a network of two-position valves which operate in conjunction with the inlet and outlet lines of the sub-beds. The fluid-directing device accomplishes moving the locations of the input and output streams through first directing the introduction or withdrawal streams to specific inlet or outlet lines of the sub-beds. After a predetermined time period called the step time, the fluid-directing device advances one index and redirects the streams to the inlet or outlet line immediately adjacent and downstream of the previously used inlet or outlet line. Each advancement of the fluid-directing device to a new position is generally called a step, and the completion of all the valve steps is called a cycle. The step time is uniform for each step in a cycle, and the cycle time ranges generally from about 15 minutes to about 3 hours.

The simulated moving bed is operated at pressures from about 5 to about 100 atm. Lower operating pressures than typically used in the prior art are possible with the current invention due to immediate and continuous removal of the product methanol. The high pressures required in the prior art were necessary to achieve a favorable shift in the equilibrium of the reaction which resulted in an increase in methanol production. In the current invention, this favorable shift is accomplished by the continuous removal of methanol from the vicinity of the active sites of the catalyst through adsorption, thus allowing for lower operating pressures.

The principal inputs and outputs of the simulated moving bed system consist of four streams: the desorbent, the feed, the extract, and the raffinate. Each stream flows into or out of the simulated moving bed at individual locations and at a particular flow rate which is independently controlled.

The feed, which is introduced to the simulated moving bed system, contains at least carbon monoxide and hydrogen, and optionally carbon dioxide, which are to undergo catalytic reaction to form methanol. Preferably, the feed is synthesis gas having a hydrogen to carbon molecular ratio in the range of about 2.0:1 to about 2.5:1, and most preferably 2.3:1. The process of the invention, as used in conjunction with synthesis gas production processes, is discussed in detail later. The f;ed is usually introduced to the simulated moving bed at a temperature of from about 210° to about 270° C. and a pressure of about 5 to about 100 atm, which are optimum temperature and pressure ranges for methanol synthesis. Once the reaction begins, however, the temperature may increase greatly since methanol synthesis is quite exothermic. To help control the temperature across the sub-beds, the feed may be separated into multiple streams. The first stream may be introduced to a sub-bed of the simulated moving bed at a temperature of about 210° to about 270° C., but subsequent feed streams would be introduced to subsequent sub-beds of the simulated moving bed at lesser temperatures to help dissipate the heat generated by the reaction. See, for example, U.S. Pat. No. 4,968,722. The feed may additionally contain other components, such as methane or nitrogen, which will be carried through the system as an impurity.

The desorbent, which is introduced to the simulated moving bed system at a pressure of about 5 to about 100 atm, is carbon dioxide, hydrogen, or methane which are all capable of displacing the selectively adsorbed methanol from adsorbents. Using carbon dioxide or hydrogen as the desorbent has several added benefits. Since the methanol is desorbed while still in the presence of the catalyst, the back reaction of methanol to carbon monoxide, carbon dioxide, and hydrogen is likely to occur. However, when the methanol is desorbed in the presence of a large volume of hydrogen or carbon dioxide, the back reaction is suppressed. Finally, by using desorbents which are also reactants, the increased conversion is facilitated and the need for an inert desorbent is eliminated. The desorbent may be derived from an independent source such as hydrogen from an ammonia production process, or the desorbent may be derived from the synthesis gas, as discussed in detail later. The back reaction may be even further suppressed by introducing the desorbent at a lower temperature. Since the hydrogenation reactions and back reactions occur optimally in the range of about 210° to about 270° C., lowering the temperature serves to quench the reactions. Accordingly, a preferred embodiment involves introducing the desorbent at a temperature in the range of about 150° to about 250° C. and preferably in the range of about 150° to about 200° C., which lowers the temperature in the immediate vicinity of the place where the methanol is being desorbed, thus quenching back reaction and maintaining overall high conversion to methanol. When using methane as the desorbent, this preferred embodiment of introducing the desorbent at a lower temperature is particularly important. Since methane is an inert compound, it will not operate to shift the equilibrium and suppress the back reaction of methanol to carbon monoxide and hydrogen. Therefore, it becomes important that the methane be introduced at a temperature lower than the optimal hydrogenation reaction temperature in order to quench the back reaction. A benefit to choosing methane as the desorbent is that the volume of inert methane flowing through the simulated moving bed operates as a heat sink and aids in controlling the temperature of the bed.

The extract and the raffinate are both withdrawn from the simulated moving bed system. The raffinate contains desorbent and unconsumed reactants which were less strongly adsorbed by the bed and were carried with the fluid flow. It is expected that substantially all of the carbon monoxide will be consumed, so the raffinate will most likely contain largely desorbent and hydrogen. When the desorbent is hydrogen, the raffinate stream may be recycled for use as desorbent or combined with the feed stream. When the desorbent is carbon dioxide, the raffinate stream, a mixture of carbon dioxide and hydrogen, may be recycled and combined with the feed stream. The extract contains desorbent and the methanol which was selectively adsorbed by the bed and then desorbed by the desorbent. The methanol is readily recovered from the methanol and desorbent mixture using a technique such as condensation followed by purification using a train of distillation towers. If carbon dioxide was present in the reaction mixture, water would also be produced and the water would proceed through the system in the same manner as the methanol; the water would be carried with the adsorbent, desorbed, and removed in the extract stream.

Typically in a commercial system, the four principal streams are spaced strategically throughout the simulated moving bed system and divide the sub-beds into three zones, each of which performs a different function. Zone I contains the sub-beds located between the feed input and the raffinate output, and the majority of the methanol synthesis reaction and the adsorption of methanol takes place in this zone. Zone II contains the sub-beds located between the extract output and the feed input, and some of the methanol synthesis reaction, the desorption of the less selectively adsorbed reactants, and the continued adsorption of the selectively adsorbed methanol takes place in this zone. Zone III contains the sub-beds located between the desorbent input and the extract output, and the selectively adsorbed methanol is desorbed in this zone. The desorption may serve to regenerate the adsorbent solids in addition to allowing the selectively adsorbed methanol to be desorbed and collected.

As discussed above, the feed of the present invention must contain at least carbon monoxide and hydrogen. This is a minimum requirement, and a wide variety of different feed compositions may be used. For example, the feed may additionally contain carbon dioxide, nitrogen, methane, or other hydrocarbons. The hydrogen to carbon molecular ratio may extend from about 2.0:1 to about 3.0:1. Therefore, the feed may be produced by an assortment of processes, the most common of which are discussed below.

The methanol production process of the present invention would typically be used in conjunction with a synthesis gas production process which would provide the feed and possibly the desorbent to the simulated moving bed. Various synthesis gas production processes exist in the prior art. The most common process involves steam reforming, or converting hydrocarbon feed into synthesis gas by reacting the hydrocarbons catalytically with steam at high temperatures. A typical hydrocarbon feed is natural gas, which is largely methane. The natural gas is first desulfurized to remove hydrogen sulfide, usually by adsorption over zinc oxide granules. Then in the presence of a nickel catalyst, steam is reacted with the natural gas at elevated temperatures and pressures to give a synthesis gas mixture of carbon dioxide, carbon monoxide, hydrogen, water, and methane according to the equations:

$$CH_4 + H_2O \rightleftharpoons CO + 3H_2O$$

$$CO + H_2O \rightleftharpoons CO_2 + H_2$$

A typical hydrogen to carbon molecular ratio of the synthesis gas from a steam reformer is from about 2.6:1 to about 2.9:1. Additional carbon dioxide may be added to bring the ratio closer to the optimum ratio for methanol synthesis of 2.3:1. The synthesis gas is passed to a condensation unit to remove water, and the water-depleted synthesis gas is then compressed to about 5 to about 100 atm and may be introduced to the simulated moving bed of the present invention where the process continues as discussed in detail above. In this embodiment, a separate source of desorbent is necessary, which would also be introduced to the simulated moving bed. Alternatively, the excess hydrogen of the synthesis gas may be separated by, for example, pressure swing adsorption and used as the desorbent.

If excess hydrogen is not needed as desorbent and hydrogen recycle is to be minimized, a secondary reforming step may also be included. The natural gas is desulfurized as above and divided into two portions. One portion is steam reformed as above to form a mixture of carbon dioxide, carbon monoxide, hydrogen, methane, and water having a hydrogen to carbon molecular ratio of about 2.6:1 to about 2.9:1. The mixture is combined with the second portion of the desulfurized natural gas and is introduced to a secondary reforming unit which is a catalytic partial oxidation or autothermal reforming unit. A stream containing oxygen is also introduced to the unit, and the following reaction occurs:

$$CH_4 + 0.5O_2 \rightleftharpoons CO + 2H_2$$

The resulting mixture of carbon dioxide, carbon monoxide, hydrogen, methane, and water has a hydrogen to carbon molecular ratio of about 2.1:1 to about 2.5:1, and preferably about 2.3:1. The stream containing oxygen may be either 80 to 100 mass % oxygen or may be air. If air is used, a substantial volume of nitrogen will be carried through the process. While the presence of nitrogen may require a larger volume simulated moving bed, the nitrogen may function to control the heat generated during methanol synthesis. The efficiency improvement due to temperature control, and the capital cost savings of not investing in an air separation unit to form relatively pure oxygen, may offset the increased cost of a larger simulated moving bed. The mixture, having the optimum hydrogen to carbon molecular ratio, is condensed to remove water and then compressed to a pressure in the range of about 5 to about 100 atm and introduced as the feed to the simulated moving bed of the invention where the process continues as discussed in detail above. Note that in this embodiment, an independent source of desorbent is required. The combined reforming using steam reforming and secondary reforming is described in S. C. Nirula, *Methanol from National Gas by the Lurgi Combined Reforming Process*, Process Economics Program, SRI International, Menle Park, Calif. October 1990, PEP Review No. 89-3-1.

While natural gas is the most preferred starting material, other hydrocarbons such as $C_5$-$C_{10}$ naphtha, $C_{13}$-$C_{20}$ fuel oil, and coal, may be used to form the feed and perhaps the desorbent for the simulated moving bed of the present invention. When starting with naphtha, fuel oil, or coal, the synthesis gas generation is performed by partial oxidation and shift conversion rather than steam reforming. The coal is usually in a solid pulverized form and is typically in a slurry with water and air. The naphtha, fuel oil, or coal is first introduced to a partial oxidation unit along with oxygen to produce a synthesis gas stream containing mostly carbon monoxide and hydrogen and having a hydrogen to carbon molecular ratio of about 1:1. The synthesis gas stream is then passed to a desulfurization unit to remove hydrogen sulfide and carbonyl sulfide. The synthesis gas stream is next upgraded to a hydrogen to carbon molecular ratio of about 2:1 by using conventional shift conversion and carbon dioxide removal. Excess water is removed in a condensation unit, and the synthesis gas is pressurized in a compression unit. The synthesis gas is then passed to the simulated moving bed of the present invention for conversion to methanol as discussed above. The excess carbon dioxide may be used as the desorbent for the simulated moving bed eliminating the need for an independent source of carbon dioxide. As a general reference, see, Kirk-Othmer, *Encyclopedia of Chemical Technology*, 3rd ed.; John Wiley & Sons: New York, 1981; Vol. 15, pp. 401–409.

Without intending any limitation on the scope of the present invention and as merely illustrative, this invention is explained below in specific terms as applied to a specific embodiment of the invention, the continuous reaction of carbon monoxide and hydrogen to form methanol using a mixture of copper-aluminum trioxide-zinc oxide catalyst, and activated alumina adsorbent in a 3:7 ratio. For ease of understanding, the process of the invention described below is limited to having eight sub-beds. The necessary apparatus is first described and then the process of the invention as applied to the embodiment is discussed.

Figure 1:
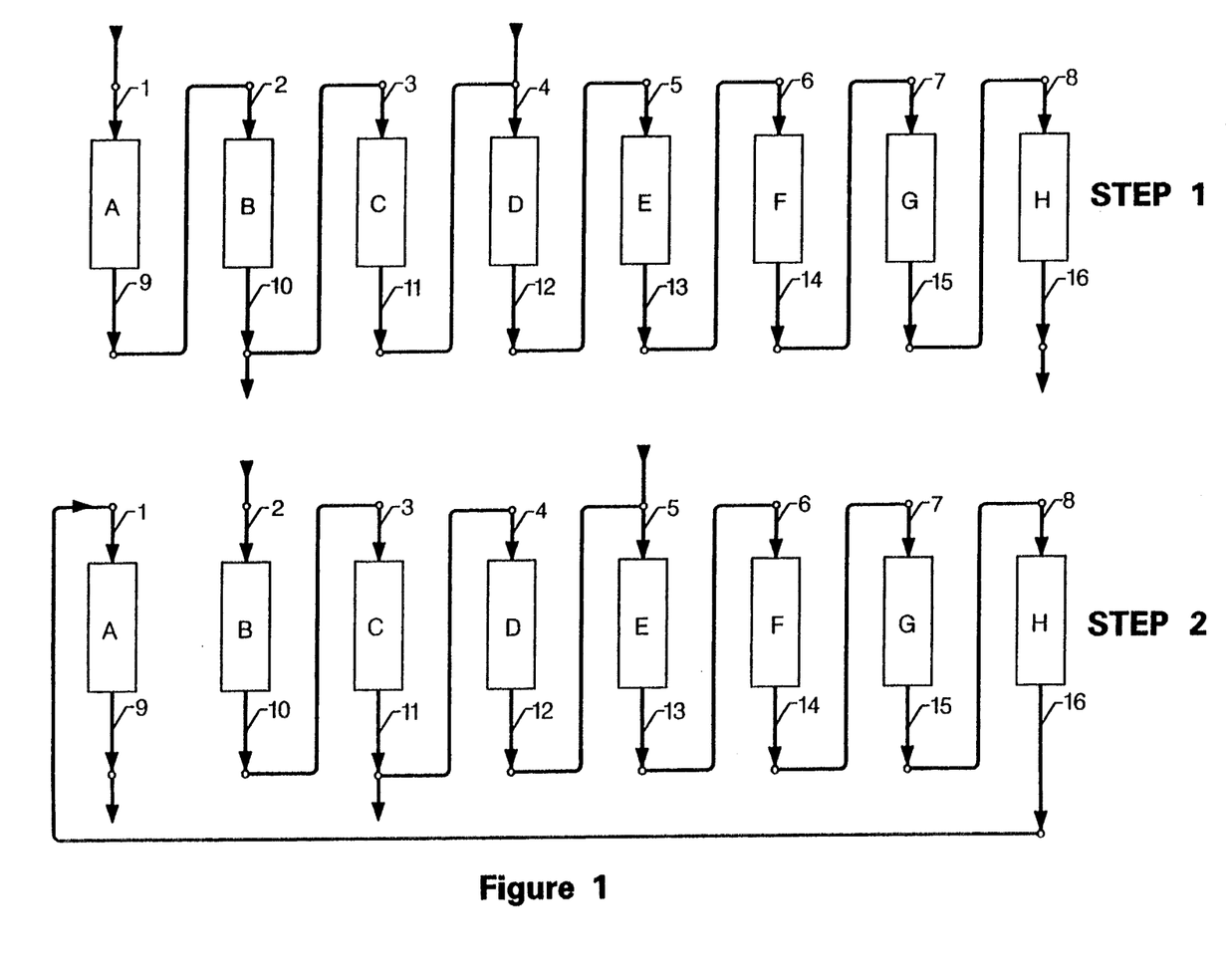
FIG. 1 contains two schematic representations of a simulated moving adsorbent and catalyst bed process at two different points in time, modified and operated in accordance with the present invention.

Referring now to FIG. 1, the simulated moving bed is made up of eight sub-beds, labeled A–H. Each sub-bed is provided with an inlet line, indicated as 1–8, and an outlet line, indicated as 9–16. Each inlet line may be used to introduce the desorbent, introduce the feed, or introduce the effluent from the previous sub-bed. Each outlet line may be used to withdraw the extract, withdraw the raffinate, or conduct the effluent to the next sub-bed. Each of the inlet and outlet lines are connected to fluid-directing and flow control apparatus (not shown). The fluid-directing apparatus allows the principal streams, the feed, the desorbent, the extract and the raffinate, to be sequentially directed to the next successive sub-bed in the direction of the fluid flow. The continued progression of the streams will simulate the movement of the solid bed in the direction countercurrent to the fluid flow. The fluid-directing apparatus also controls the interconnection of the sub-beds.

The upper diagram, labeled Step 1, shows the inlet and outlet lines at the starting position. The desorbent is introduced to the simulated moving bed through inlet line 1, and the feed is introduced to the simulated moving bed through inlet line 4. The extract is withdrawn from the simulated moving bed through outlet line 10 and the raffinate is withdrawn from the simulated moving bed through outlet line 16. The effluent of sub-beds A through G are conducted through the outlet line of each sub-bed, lines 9–15 respectively, and connected to the inlet line of the next successive sub-bed, lines 2–8 respectively, in order to conduct the effluent from sub-bed to sub-bed. The effluent of the sub-bed from which the raffinate is withdrawn, H, is not routed to the next successive sub-bed since the entire effluent is collected as the raffinate.

To demonstrate the progression of the simulated moving bed, the lower diagram, labeled Step 2, shows the configuration of the lines after the fluid-directing apparatus has advanced one step. Now the desorbent is introduced to the simulated moving bed through inlet line 2, and the feed is introduced to the simulated moving bed through inlet line 5. The extract is withdrawn from the simulated moving bed through outlet line 11 and the raffinate is withdrawn from the simulated moving bed through outlet line 9. The effluent of sub-beds B through H are conducted through the outlet line of each sub-bed, lines 10–16 respectively, and connected to the inlet line of the next successive sub-bed, lines 3–8 and line 1 respectively, in order to conduct the effluent from sub-bed to sub-bed. The effluent of the sub-bed from which the raffinate is withdrawn, A, is not routed to the next successive sub-bed since the entire effluent is collected as the raffinate. Each successive step of the fluid-directing apparatus would advance the location of the streams in a similar manner.

Using the described apparatus, the invention is performed as follows. The flow rates of each of the principal streams and the step time of fluid-directing apparatus may be first set to selected values based on the operator's experience. Due to the cyclic nature of the process the starting position of the location of the streams is not important; for this illustration the starting positions of the streams are as depicted in the diagram labeled Step 1. For ease of understanding, and specific to FIG. 1, the simulated movement of the solids may be considered as to be to the left, and the fluid flow may be considered to be to the right. When the feed containing the carbon monoxide and hydrogen reactants, conducted in inlet line 4 and at a temperature of about 210° to about 270° C., enters the simulated moving bed sub-bed D and contacts the homogeneous mixture of catalyst and adsorbent, the methanol synthesis reaction is catalyzed and methanol is formed. The carbon monoxide and hydrogen which are weakly adsorbed by the adsorbent are carried with the fluid flow. As the reactants are carried with the fluid flow, they continue to react and produce methanol. It is expected that the carbon monoxide will be completely consumed, and the excess hydrogen will be withdrawn from the bed in the raffinate stream conducted from sub-bed H in outlet line 16. The methanol which is adsorbed by the adsorbent is carried with the solid bed in its countercurrent simulated movement thereby being separated from the reactants. The methanol is desorbed from the adsorbent by the carbon dioxide desorbent which is conducted to sub-bed A through inlet line 1. The carbon dioxide is introduced at a temperature of about 150° to about 250° C. to suppress the desorbed methanol from reacting back to form carbon monoxide and hydrogen. The methanol and some desorbent are withdrawn from the sub-bed B in the extract stream conducted through outlet line 10. Some of the carbon dioxide will react to form methanol as it travels through the simulated moving bed, but the majority of the desorbent will be withdrawn in the raffinate stream conducted from sub-bed H in outlet line 16. After the predetermined step time has elapsed, the fluid-directing apparatus advances one step and the process continues.

It must be emphasized that the above description is merely illustrative of an embodiment and is not intended as an undue limitation on the generally broad scope of the invention. Moreover, while the description is narrow in scope, one skilled in the art will understand how to extrapolate to the broader scope of the invention. For example, operation of the invention where the feed stream is divided into multiple streams, each being introduced to a separate sub-bed, or where a heat exchanger is provided between each sub-bed to remove excess heat can be readily extrapolated from the foregoing description. Similarly, one skilled in the art would understand how the above process is applied to the situation where all the sub-beds are housed in a single chamber, or where streams containing desorbent are recycled. Furthermore, the optimum number of sub-beds, the optimum cycle time, and the optimum flow rates for a given application would be readily determined by one skilled in the art.

Figure 2:
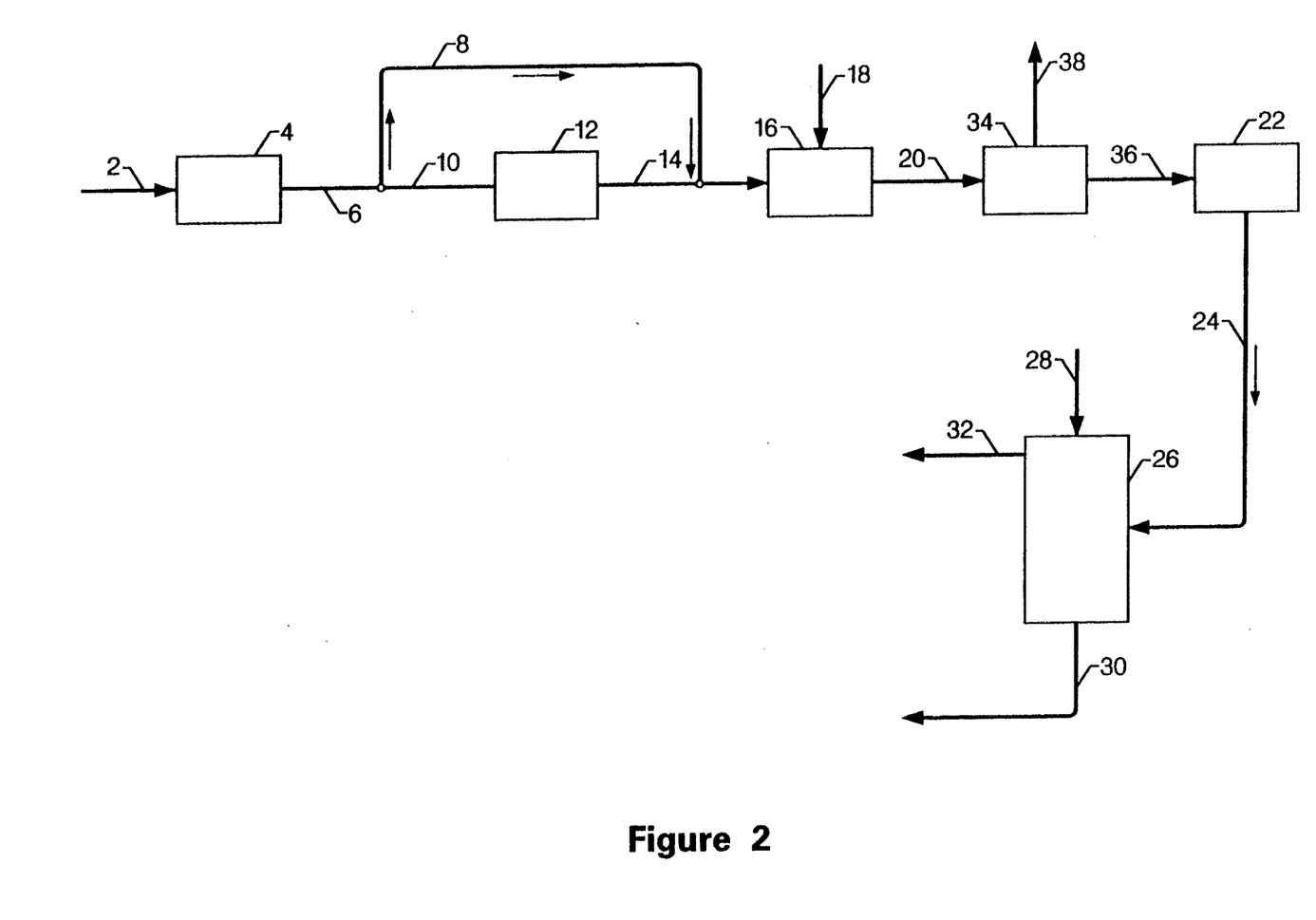
FIG. 2 is a schematic representation of a methanol production process incorporating synthesis gas generation to provide the feed to the methanol synthesis zone.

Turning now to FIG. 2, the invention is explained below in terms of the specific embodiment where methane is converted to synthesis gas with a hydrogen to carbon molecular ratio in the optimum range for methanol synthesis, and the synthesis gas is introduced to a methanol synthesis zone containing a simulated moving bed of a mixture of solids to produce and separate methanol. A natural gas stream containing largely methane, conducted in line 2, is introduced to desulfurization zone 4 containing zinc oxide granules. Hydrogen sulfide is removed by adsorption on the zinc oxide granules to produce a desulfurized methane-containing stream conducted in line 6. The stream in line 6 is divided into two portions, one portion being conducted in line 8, and one portion being conducted in line 10. The portion conducted in line 10 is introduced to steam reforming zone 12 containing a nickel catalyst and operating at about 700° C. and about 40 atm, and is reacted with steam to form a mixture of carbon monoxide, carbon dioxide, hydrogen and methane, having a hydrogen to carbon molecular ratio of from about 2.6:1 to about 2.9:1 which is conducted in line 14. The desulfurized methane portion in line 8 is combined with the stream in line 14, and the combination is introduced to secondary reforming zone 16 operating at about 1000° C. and about 40 atm. A 95 mass % oxygen stream is also introduced to secondary reforming zone 16 and the methane is converted to carbon monoxide and hydrogen. The effluent of the secondary reforming zone 16 containing a mixture of carbon monoxide, carbon dioxide, hydrogen, water, and methane having a hydrogen to carbon molecular ratio of from about 2.0:1 to about 2.5:1 is conducted in line 20 to condensation zone 34. In condensation zone 34, water is condensed from the mixture and removed in line 38 resulting in a water-depleted mixture of carbon monoxide, carbon dioxide, hydrogen and methane which is conducted in line 36 to compression zone 22. The mixture is pressurized to about 20 atm in the compression zone and conducted through line 24 to methanol synthesis zone 26. Carbon dioxide desorbent is also introduced to methanol synthesis zone 26 through line 28. The apparatus and operation of methanol synthesis zone 26 is described in detail above in reference to FIG. 1. Methanol produced in the, methanol synthesis zone and some carbon dioxide desorbent is conducted from the methanol synthesis zone in line 32 and collected. Hydrogen and carbon dioxide are conducted from the methanol synthesis zone in line 30.

It must be emphasized that the above description is merely illustrative of an embodiment and is not intended as an undue limitation on the generally broad scope of the invention. Moreover, while the description is narrow in scope, one skilled in the art will understand how to extrapolate to the broader scope of the invention. For example, operation of the invention where no secondary reforming is used, or where hydrogen instead of carbon dioxide is used as the desorbent, can be readily extrapolated from the foregoing description. Furthermore, operation of the invention with the recycling of streams containing desorbent would be readily apparent to one skilled in the art.

What is claimed is:

1. A process for the continuous production of methanol comprising:
    a. continuously introducing into a simulated moving bed of particulate solids containing at least a catalyst for the reaction of carbon monoxide and hydrogen and an adsorbent to selectively adsorb methanol relative to the carbon monoxide and hydrogen, a desorbent and at least one feed stream containing at least carbon monoxide and hydrogen;
    b. reacting at least a portion of the carbon monoxide and hydrogen to form methanol in a zone of the simulated moving bed with concurrent separation of the methanol formed in the zone from the carbon monoxide and hydrogen using the adsorbent;
    c. continuing the reaction of the carbon monoxide and hydrogen in a first successive zone of the simulated moving bed with concurrent separation of methanol formed thereby using the adsorbent; and
    d. recovering methanol from the adsorbent using the desorbent in a second successive zone of the simulated moving bed.

2. The process of claim 1 where the catalyst is selected from the group consisting of zinc oxide-chromium trioxide, copper-zinc oxide-chromium trioxide, copper-zinc oxide, copper-zinc oxide-aluminum trioxide, copper oxide-zinc oxide-aluminum trioxide, and zinc-chromium trioxide, and the adsorbent is selected from the group consisting of aluminum trioxide, silica gel, 3A-, 4A-, 5A-, X-, and Y-type zeolites, ZSM-5, activated carbon, ferrurite, and high aluminum MCM-41.

3. The process of claim 1 where the catalyst and adsorbent are present in a ratio of about 1:9 to about 9:1.

4. The process of claim 3 where the desorbent is hydrogen and the adsorbent is 3A-type zeolite.

5. The process of claim 1 where the catalyst and adsorbent are present in a ratio of about 1:1 to about 1:5.

6. The process of claim 5 where the catalyst and adsorbent are present in a ratio of about 1:3, and the adsorbent is aluminum trioxide.

7. The process of claim 1 where the desorbent is selected from the group consisting of hydrogen, carbon dioxide, and methane.

8. The process of claim 1 where the feed stream containing at least carbon monoxide and hydrogen is introduced to the simulated moving bed at a temperature from about 210° to about 270° C. and where the desorbent is carbon dioxide which is introduced to the simulated moving bed at a temperature of about 150° to about 250° C.

9. A process for the continuous production of methanol comprising:
   a. passing a methane-containing stream to a desulfurization zone to form a desulfurized methane-containing stream which is depleted in hydrogen sulfide;
   b. passing the desulfurized methane-containing stream to a steam reforming zone where the methane is reacted with water to form carbon monoxide and hydrogen, and a portion of the carbon monoxide is further reacted with water to form carbon dioxide and hydrogen, resulting in a stream containing at least carbon monoxide, carbon dioxide, hydrogen, and water;
   c. passing the stream containing at least carbon monoxide, carbon dioxide, hydrogen, and water to a condensation zone to remove water resulting in a water-depleted stream containing at least carbon monoxide, carbon dioxide, and hydrogen;
   d. passing the water-depleted stream containing at least carbon monoxide, carbon dioxide, and hydrogen to a compression zone to afford a pressurized stream containing at least carbon monoxide, carbon dioxide, and hydrogen;
   e. passing the pressurized stream containing at least carbon monoxide, carbon dioxide, and hydrogen and a stream containing a desorbent selected from the group consisting of carbon dioxide, hydrogen, and methane to a methanol synthesis zone of a simulated moving bed to produce a stream containing methanol and desorbent, and a stream containing at least hydrogen and desorbent;
   f. passing the stream containing methanol and desorbent to a separation zone to produce a stream enriched in methanol and a stream enriched in desorbent; and
   g. collecting the stream enriched in methanol.

10. The process of claim 9 where the stream enriched in desorbent is recycled.

11. The process of claim 9 where the stream containing at least hydrogen and desorbent is recycled.

12. The process of claim 9 where the stream enriched in desorbent and the stream containing at least hydrogen and desorbent are recycled.

13. A process for the continuous production of methanol comprising:
   a. passing a methane-containing stream to a desulfurization zone to form a desulfurized methane-containing stream which is depleted in hydrogen sulfide;
   b. dividing the desulfurized methane-containing stream into two portions, the first portion being passed to a steam reforming zone where the methane is reacted with water to form carbon monoxide and hydrogen, and a portion of the carbon monoxide is reacted with water to form carbon dioxide and hydrogen, resulting in a steam reforming zone effluent containing a mixture of carbon monoxide, carbon dioxide, hydrogen, and water, which is combined with the second portion of the desulfurized methane-containing stream to form a stream containing methane, carbon monoxide, carbon dioxide, hydrogen, and water;
   c. passing the stream containing methane, carbon monoxide, carbon dioxide, hydrogen, and water and a stream containing oxygen to a catalytic reforming zone where methane is reacted with oxygen to form carbon monoxide and hydrogen to afford a stream containing at least carbon monoxide, carbon dioxide, hydrogen, and water which has a hydrogen to carbon molecular ratio in the range of about 2.0:1 to about 2.5:1;
   d. passing the stream containing at least carbon monoxide, carbon dioxide, hydrogen, and water to a condensation zone to afford a water-depleted stream containing at least carbon monoxide, carbon dioxide, and hydrogen;
   e. passing the water-depleted stream containing at least carbon monoxide, carbon dioxide, and hydrogen to a compression zone to afford a pressurized stream containing at least carbon monoxide, carbon dioxide, and hydrogen;
   f. passing the pressurized stream containing at least carbon monoxide, carbon dioxide, and hydrogen, and a stream containing a desorbent selected from the group consisting of carbon dioxide, hydrogen, and methane to a methanol synthesis zone of a simulated moving bed to produce an extract stream containing methanol and desorbent, and a raffinate stream containing at least hydrogen and desorbent;
   g. passing the stream containing methanol and desorbent to a separation zone to produce a stream enriched in methanol and a stream enriched in desorbent; and
   h. collecting the stream enriched in methanol.

14. The process of claim 13 where the stream enriched in desorbent and the raffinate stream are recycled.

15. The process of claim 13 where the stream enriched in desorbent is recycled.

16. The process of claim 13 where the raffinate stream is recycled.

17. The process of claim 13 where the oxygen-containing stream contains from 80 to 100 mass % oxygen.

18. The process of claim 13 where the oxygen-containing stream is air, and the raffinate stream further comprises at least nitrogen.

19. A process for the continuous production of methanol comprising:
   a. passing a methane-containing stream to a desulfurization zone to form a desulfurized methane-containing stream which is depleted in hydrogen sulfide;
   b. passing the desulfurized methane-containing stream to a steam reforming zone where the methane is reacted with water to form carbon monoxide and hydrogen, and a portion of the carbon monoxide is reacted with water to form carbon dioxide and hydrogen, resulting in a stream containing at least carbon monoxide, carbon dioxide, hydrogen, and water;

c. passing the stream containing at least carbon monoxide, carbon dioxide, hydrogen, and water to a condensation zone to afford a water-depleted stream containing at least carbon monoxide, carbon dioxide, and hydrogen;
d. passing the water-depleted stream containing at least carbon monoxide, carbon dioxide, and hydrogen to a compression zone to afford a pressurized stream containing at least carbon monoxide, carbon dioxide, and hydrogen;
e. passing the pressurized stream containing at least carbon monoxide, carbon dioxide, and hydrogen to a first separation zone to afford a first stream enriched in hydrogen and a stream enriched in carbon monoxide and hydrogen having a hydrogen to carbon molecular ratio of from about 2.0:1 to about 2.5:1;
f. passing the first stream enriched in hydrogen and the stream enriched in carbon monoxide and hydrogen to a methanol synthesis zone of a simulated moving bed to produce a stream containing methanol and hydrogen, and a second stream containing hydrogen;
g. passing the stream containing methanol and hydrogen to a second separation zone to produce a stream enriched in methanol and a third stream enriched in hydrogen; and
h. collecting the stream enriched in methanol.

20. The process of claim 19 where the second and third streams enriched in hydrogen are recycled and combined with the first stream enriched in hydrogen.

21. A process for the continuous production of methanol comprising:
a. passing a naphtha-, fuel oil-, or coal-containing stream and an oxygen-containing stream to a partial oxidation zone to form a stream containing at least carbon monoxide and hydrogen;
b. passing the stream containing at least carbon monoxide and hydrogen to a desulfurization zone to form a desulfurized stream containing carbon monoxide and hydrogen which is depleted in hydrogen sulfide;
c. passing the desulfurized stream containing at least carbon monoxide and hydrogen to a shift conversion reaction zone where at least a portion of the carbon monoxide is reacted with water to form carbon dioxide and hydrogen thereby forming a stream of at least carbon monoxide, carbon dioxide, hydrogen, and water;
d. passing the stream containing at least carbon monoxide, carbon dioxide, hydrogen, and water to a condensation zone to afford a water-depleted stream containing at least carbon monoxide, carbon dioxide, and hydrogen;
e. passing the water-depleted stream containing at least carbon monoxide, carbon dioxide, and hydrogen to a compression zone to afford a pressurized stream containing at least carbon monoxide, carbon dioxide, and hydrogen;
f. passing the pressurized stream containing at least carbon monoxide, carbon dioxide, and hydrogen to a first separation zone to afford a first stream enriched in carbon dioxide and a stream enriched in carbon monoxide and hydrogen and having a hydrogen to carbon molecular ratio of from about 2.0:1 to about 2.5:1;
g. passing the first stream enriched in carbon dioxide and the stream enriched in carbon monoxide and hydrogen to a methanol synthesis zone of a simulated moving bed to produce a stream containing methanol and carbon dioxide, and a second stream containing hydrogen and carbon dioxide;
h. passing the stream containing methanol and carbon dioxide to a second separation zone to produce a stream enriched in methanol and a second stream enriched in carbon dioxide; and
i. collecting the stream enriched in methanol.

22. The process of claim 21 where the second and third streams enriched in hydrogen are recycled and combined with the first stream enriched in hydrogen.

* * * * *